United States Patent
Toulhoat et al.

(10) Patent No.: US 9,101,919 B2
(45) Date of Patent: Aug. 11, 2015

(54) OLEFIN OLIGOMERIZATION METHOD INVOLVING A CATALYTIC SYSTEM BASED ON ORGANOMETALLIC COMPLEXES AND A POROUS SOLID

(75) Inventors: Herve Toulhoat, Herblay (FR); Theodorus De Bruin, Paris (FR); Pascal Raybaud, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 1259 days.

(21) Appl. No.: 12/994,958

(22) PCT Filed: Apr. 29, 2009

(86) PCT No.: PCT/FR2009/000510
§ 371 (c)(1),
(2), (4) Date: Feb. 15, 2011

(87) PCT Pub. No.: WO2009/144410
PCT Pub. Date: Dec. 3, 2009

(65) Prior Publication Data
US 2011/0137100 A1   Jun. 9, 2011

(30) Foreign Application Priority Data
May 30, 2008 (FR) ..................... 08 02977

(51) Int. Cl.
| | |
|---|---|
| *C07C 2/24* | (2006.01) |
| *B01J 31/22* | (2006.01) |
| *B01J 31/06* | (2006.01) |
| *B01J 31/16* | (2006.01) |
| *B82Y 30/00* | (2011.01) |
| *C07C 2/32* | (2006.01) |
| *C07C 2/34* | (2006.01) |
| *B01J 21/18* | (2006.01) |
| *B01J 29/04* | (2006.01) |
| *B01J 29/06* | (2006.01) |
| *B01J 29/08* | (2006.01) |
| *B01J 29/70* | (2006.01) |
| *B01J 29/83* | (2006.01) |

(52) U.S. Cl.
CPC ............ *B01J 31/2295* (2013.01); *B01J 31/069* (2013.01); *B01J 31/1691* (2013.01); *B82Y 30/00* (2013.01); *C07C 2/32* (2013.01); *C07C 2/34* (2013.01); *B01J 21/185* (2013.01); *B01J 29/041* (2013.01); *B01J 29/06* (2013.01); *B01J 29/08* (2013.01); *B01J 29/70* (2013.01); *B01J 29/83* (2013.01); *B01J 2229/34* (2013.01); *B01J 2231/20* (2013.01); *C07C 2529/08* (2013.01); *C07C 2529/83* (2013.01); *C07C 2531/22* (2013.01)

(58) Field of Classification Search
CPC ........ C07C 2/32; C07C 2/34; C07C 2529/08; C07C 2529/83; C07C 2531/22; B01J 21/185; B01J 2229/34; B01J 2231/20; B01J 29/041; B01J 29/06; B01J 29/08; B01J 29/70; B01J 29/80; B01J 29/83
USPC ................. 585/500, 502, 510, 511, 512
See application file for complete search history.

(56) References Cited

U.S. PATENT DOCUMENTS

| | | | |
|---|---|---|---|
| 5,869,417 A | 2/1999 | Woo et al. | |
| 6,930,193 B2 * | 8/2005 | Yaghi et al. | ...... 556/46 |
| 7,384,886 B2 * | 6/2008 | Knudsen et al. | ...... 502/167 |
| 2004/0220165 A1 | 11/2004 | Thomas et al. | |
| 2005/0215792 A1 * | 9/2005 | De Boer et al. | ...... 546/2 |

FOREIGN PATENT DOCUMENTS

WO   WO 2008140788 A1 * 11/2008 .............. C01B 39/00

OTHER PUBLICATIONS

Weitkamp. "Zeolites and Catalysis" in Solid State Ionics, 131 (2000) 175-188—month unknown.*
Tobisch, et al., "Catalytic Linear Oligomerization of Ethylene to Higher α-Olefins: Insight into the Origin of the Selective Generation of 1-Hexene Promoted by a Cationic Cyclopentadienyl-Arene Titanium Active Catalyst" in Organometallics, 2003, 22, 5392-5405—Nov. 2003.*
International Search Report of PCT/FR2009/000510 (Oct. 28, 2009).
M. O. De Souza et al., "A Nano-Organized Ethylene Oligomerization Catalyst: Characterization and Reactivity of the Ni(MeCN)6(BF4)2/[Al]-MCM-41/AlEt3 System", Microporous and Mesoporous Materials, vol. 96 (2006) pp. 109-114.
P. J. W. Deckers et al., "Catalytic Trimerization of Ethene with Highly Active Cyclopentadienyl-Arene Titanium Catalysts", Organometallics, vol. 21 (2002) pp. 5122-5135.
Y. Guo et al., "Organic-Inorganic Hybrid Supported Zirconocene Catalysts for Ethylene Polymerization", Journal of Molecular Catalysis A: Chemical, vol. 237 (2005) pp. 45-49.

* cited by examiner

*Primary Examiner* — Walter D Griffin
*Assistant Examiner* — Ali Z Fadhel
(74) *Attorney, Agent, or Firm* — Millen, White, Zelano & Branigan P.C.

(57) ABSTRACT

The present invention relates to a method of oligomerizing olefins M selectively to oligomers $M_n$, involving a catalytic system comprising at least one organometallic complex with a metal of groups 4 to 10 of the periodic table of molecular volume $Vm_o$, and a micro- or mesoporous solid whose average micropore diameter $\Phi$ is greater than or equal to $\Phi_{min}$ defined as a function of the molecular volume ($Vm_o + nVm_M$), where n is the number of monomeric olefins strung together upon obtaining the metallacycle intermediate and $Vm_M$ the molecular volume of the monomeric olefin.

14 Claims, No Drawings

US 9,101,919 B2

OLEFIN OLIGOMERIZATION METHOD INVOLVING A CATALYTIC SYSTEM BASED ON ORGANOMETALLIC COMPLEXES AND A POROUS SOLID

FIELD OF THE INVENTION

The invention relates to an olefin oligomerization method wherein the catalytic system used comprises at least one organometallic complex of a metal of groups 4 to 10 of the periodic table and a micro- or mesoporous solid.

BACKGROUND OF THE INVENTION

A recurrent handicap of the methods based on molecular (or homogeneous) catalysis lies in the difficulty in separating the products and the catalyst in order to recycle the latter. In most cases, these methods work on a lost catalyst basis with, in addition, the potential problem of toxicity of the catalytic species present, even as traces, in the products. "Heterogenization" of homogeneous catalysts is thus a problem widely studied. One possible way consists in immobilizing the catalytic species on or in a support, notably mineral.

The article by Zhao et al. (*Materials Today*, 9, 3, p. 32-39, 2006) reviews several molecular catalyst and enzyme immobilization modes, and it notably mentions chemical grafting, electrostatic grafting, adsorption and encapsulation. Immobilization by adsorption is essentially based on the Van der Waals forces alone, and it is notably very frequently used to immobilize enzymes in ordered mesoporous materials. In fact, this type of immobilization is simple and requires no treatment of the support, which allows not to denature the enzyme.

The worldwide demand for alpha-olefins, intermediaries used in the manufacture of surfactants, additives for lubricants and fuel bases, continues to grow. There are several commercial methods of oligomerizing ethylene to hexene-1 by molecular catalysis and a considerable amount of work is available today on the modification of these systems in order to direct them towards the selective production of octene-1 or higher oligomers.

The article by Deckers et al. (*Angew. Chem. Int. Ed.* 2001, 40, 2516-2519) presents an organometallic complex wherein the $Ti^+$ ion is coordinated by a hemilabile ligand $\eta^5$-$C_5H_4CMe_2C_6H_5$ and used to selectively produce hexene-1, the co-catalyst used being methylaluminoxane (MAO). The reaction flowsheet corresponding to the trimerization of ethylene in a method using this organometallic complex as the catalyst is detailed in the article by T. de Bruin et al. (*Organometallics*, 2003, 22, 3404-3413). The mechanism that seems to be well established today involves a succession of metallacycle intermediates and of transition states. For each metallacycle intermediate obtained upon ethylene oligomerization, there is either a possibility of cycle opening through hydrogen transfer, subsequently leading to the desorption of the corresponding alpha-olefin (butene-1, hexene-1, octene-1 or decene-1, respectively for 2, 3, 4 and 5 ethylene molecules strung together), or a possibility of growth of the metallacycle intermediate by two additional links through the insertion of a new ethylene molecule.

It is of particular interest to be able to influence the reactivity by acting on the activity and the selectivity of the catalytic system in order to selectively obtain an alpha-olefin such as, for example, octene-1 or decene-1. The present invention, which furthermore allows easy separation for recycle of at least part of the catalytic system, falls within this scope.

DETAILED DESCRIPTION

The present invention relates to a method of oligomerizing olefins M selectively to oligomers $M_n$, involving a catalytic system comprising at least one organometallic complex of a metal of groups 4 to 10 of the periodic table of molecular volume $Vm_o$, and a microporous or mesoporous solid, selected from among zeolites, organic-inorganic hybrid materials, mesoporous materials such as MCM, SBA, or carbon nanotubes, and whose pore diameter $\Phi$ expressed in nm is greater than or equal to $\Phi_{min}$ defined as a function of the volume $(Vm_o+nVm_M)$, expressed in $nm^3$, where n is the number of monomeric olefins strung together upon obtaining the metallacycle intermediate and $Vm_M$ the molecular volume of the monomeric olefin, the relation between diameter $\Phi_{min}$ and volume $(Vm_o+nVm_M)$ being written as follows:

$$\Phi_{min}=1.579(Vm_o+nVm_M)^{1/3}-0.323$$

Molecular volume Vm is an easily calculatable descriptor for a fixed molecular geometry. It is defined as the volume delimited by the envelope surface of the Van der Waals spheres centered on the atomic nuclei belonging to the molecule in its geometry in the fundamental state as given by a crystallographic experiment or an ab initio theoretical calculation.

The average pore diameter $\Phi$ is defined as the arithmetic mean of the maximum and minimum free crystallographic diameters given in "Atlas of zeolite framework types" by Ch. Baerocher, W. M. Meier and D. H. Olson, edited by Elsevier on behalf of the "Structure Commission of the International Zeolites Association", 5th revision published in 2001, available for free download at: http://www.iza-structure.org/. These values are deduced from the crystallographic positions of the framework oxygen atoms in the asymmetric crystallographic cell by determining the corresponding diametrically opposite atoms that make up the pore walls and by subtracting from the distance between these atoms the Van der Waals diameter of an $O^2$ ion equal, by convention, to 0.27 nm. In the case of the faujasite structure, the maximum diameter is the diameter of a supercage, i.e. 1.18 nm, and the minimum diameter is 0.74 nm: the average diameter consequently is 0.96 nm.

The relation between diameter $\Phi_{min}$ and volume $(Vm_o+nVm_M)$ is written as follows:

$$\Phi_{min}=1.579(Vm_o+nVm_M)^{1/3}-0.323$$

Preferably, the pore diameter $\Phi$ of the micro- or mesoporous solid is less than $3*\Phi_{min}$ and preferentially ranges between $1.01*\Phi_{min}$ and $1.64*\Phi_{min}$.

More preferably, the pore diameter $\Phi$ of the said solid ranges between $1.05*\Phi_{min}$ and $1.25*\Phi\Phi_{min}$.

The activity and the selectivity of the catalytic system used in the method according to the present invention are notably determined by the free energy barriers to overcome for each of the possible reaction paths (growth of the metallacycle intermediate or opening through hydrogen transfer).

Thus, by modifying the free energy barriers, it becomes possible to orient the selectivity towards a particular oligomer $M_n$ and to improve the activity of the catalytic system involved in the method according to the invention. This modification is made possible by the physical adsorption, determined notably by the Van der Waals forces, of a molecular species such as a metallacycle intermediate or transition state in a pore or a cavity whose radius of curvature is slightly greater than that of the Van der Waals envelope of this molecule.

For a porous solid of given pore radius, a stabilization of the adsorbed species increasing with the molecular size is observed, up to a maximum size beyond which the steric constraints preclude adsorption.

The size differences between the various metallacycle reaction intermediates and transition states involved during the oligomerization reaction are translated into a differentiated stabilization.

According to the present invention, if the stabilization of one of the metallacycle reaction intermediates or transition states is sufficiently increased in relation to that of another intermediate, through optimized adsorption in a pore of the solid, the order of amplitude of the energy barriers can be modified: it is thus possible to favour the production of an oligomer rather than another.

In the particular case of the ethylene oligomerization reaction, it is thus possible to favour for example the production of octene-1 in relation to hexene-1.

From the optimized geometries at 0K obtained by DFT (Density Functional Theory) for the metallacycle intermediates and transition states, the molecular volumes were calculated by means of the QSAR (Quantitative Structure Activity Relationships) tools of Accelrys' molecular modelling platform Materials Studio 4.3.

In the case of the organometallic complex wherein the $Ti^+$ ion is coordinated by a hemilabile ligand $\eta^5$-$C_5H_4CMe_2C_6H_5$, referred to as Teuben complex hereafter, the Van der Waals radii taken into account are 0.13, 0.20 and 0.195 nm for H, C and $Ti^+$ respectively.

The molecular volume $Vm_o$ corresponds to the volume of the organometallic complex used as catalyst.

Volume ($Vm_o+nVm_M$) practically corresponds to the molecular volume of the metallacycle reaction intermediate or transition state wherein n molecules of monomeric olefins of molecular volume $Vm_M$ have been strung together.

The micro- or mesoporous materials used within the scope of the present invention are materials having sufficiently large pores for a molecular species to be adsorbed therein. Preferably, these materials are zeolites, organic-inorganic hybrid materials (or MOF for Metal Organic Framework) such as IRMOF, MIL or ZIF, mesoporous materials such as MCM, SBA, or carbon nanotubes.

Zeolites of CFI, AFI, MAZ, AET, DON, FAU, CLO or VFI type described in the IZA data base are preferably selected from among the zeolites. IRMOF or ZIF materials are preferably selected from among the organic-inorganic hybrid materials More preferably, the said solid is a MOF of IRMOF-1 type or a ZIF of ZIF-60 type.

The catalytic system used in the method according to the present invention is such that it comprises at least one metallic cation selected from groups 4 to 10 belonging to the organometallic complex for a cation constitutive of the microporous or mesoporous solid.

EXAMPLES

Example 1

Not in Accordance with the Invention, without Micro- or Mesoporous Solid

Oligomerization of Ethylene Catalyzed by the Teuben Complex [($\eta^5$-$C_5H_4CMe_2C_6H_5$)$Ti^+$]

The procedure is precisely as described in the article by Decker et al. (*Organometallics* 2002, 21, 5122-5135) for the trimerization of ethylene by the catalyst resulting from the activation of the complex [($\eta^5$-$C_5H_4CMe_2C_6H_5$)$TiCl_3$] by the MAO (methylaluminoxane): the ligand ($\eta^5$-$C_5H_4CMe_2C_6H_5$) is synthesized as indicated in the article by reacting the fulvene with phenyl-lithium chloride so as to obtain the corresponding lithium cyclopentadienide. The precursor P [($\eta^5$-$C_5H_4CMe_2C_6H_5$)$TiCl_3$] is then obtained by reaction with $TiCl_4$. A pressure and temperature regulated 1 L-autoclave reactor equipped with solvent and catalyst injection systems is preheated under vacuum for 60 min to 120° C. so as to desorb any impurity from the walls and the internal structures. It is subsequently cooled to the temperature selected for the experiment, equal to 30° C. 200 ml anhydrous toluene of purity above 99.9%, further purified by passage through alumina, then passage through a copper-based oxygen capture catalyst (BASF R3-11), then a 4 A molecular sieve, all of it under U nitrogen atmosphere, are added, and the reactor is pressurized to 2 bars ethylene pressure itself purified by passage through BASF R3-11 and A4 sieve. After 30-min balancing, 30 ml of a MAO solution are injected into the toluene at 0.5 mole aluminium per litre. At the zero reaction time, 1 ml of a 15 millimolar solution of precursor P is injected into the toluene, blended with 2 g cyclooctane used as internal standard for analyses, then 30 ml toluene are injected. The Al/Ti molar ratio is thus substantially set at 1000. The reaction starts, consuming ethylene whose pressure is maintained at 2 bars±0.1 bar. The reaction is stopped after the time t=30 min by addition of ethanol, the reactor is depressurized and scavenged under argon at atmospheric pressure. 25 more ml ethanol are added to destroy the residual MAO and liquid phase samples are taken for gas chromatography analysis. The high molecular weight reaction products are separated from the liquid effluents by Rotavapor evaporation.

The balance leads to identify substantially 9.3 g reaction products, including 8.20 g $C_6$ products (88.08%) with 99.5% hexene-1, 0.01 g (0.11%) $C_8$ products with 99.5% octene-1, 0.90 g (9.67%) $C_{10}$ products with 85% 5-methyl-non-1-ene and 0.20 g (2.15%) polyethylene. The 5-methyl-non-1-ene results, as shown in the article, from the cotrimerization of hexene-1 and ethylene. These results substantially reproduce those of the article. Assuming, as in the article, the prevalence of an order 1 in relation to ethylene, the hexene-1 productivity is thus established at 547 g per millimole of Ti per bar and per hour, the hexene-1 selectivity is 87.6% and the octene-1 selectivity is 0.11%.

Example 2

According to the Invention

Oligomerization of Ethylene Catalyzed by the Teuben Complex [($\eta^5$-$C_5H_4CMe_2C_6H_5$)$Ti^+$] in the Presence of a Porous Solid of AET Structure (ALPO-8)

The procedure is the same as in Example 1, except for the initial introduction of 200 ml of a 4.56-mg/l AET suspension (AlPO-8) in toluene instead of pure toluene. This solid was synthesized according to the operating mode described in the article by Dessau, R. M., Schlenker, J. L. and Higgins, J .B. (*Zeolites*, 10, 522-524 (1990)). The chemical composition of this material is $A_{36}P_{36}O_{144}$. The amount added thus corresponds to 15/72 micromoles of crystallized solid cells, i.e. substantially 1 constitutive cation ($Al^{3+}$ or $P^{5+}$) per $Ti^+$ in the reaction medium.

The reaction is stopped after 60 seconds. Analysis of the reaction products shows that the hexene-1 productivity was multiplied by 2.1, thus reaching 1142 g per millimole of Ti per bar and per hour, whereas the octene-1 productivity now reaches 219 000 g per millimole of Ti per bar and per hour (i.e. substantially 110 g $C_8$ products).

The average micropore diameter of the AET structure taken from the IZA atlas is $\Phi=(0.79+0.87)/2=0.83$ nm.

The molecular volume of the complex $[(\eta^5\text{-}C_5H_4CMe_2C_6H_5)Ti^+]$ was calculated from the coordinates of the stable form at OK published in the article by Theodorus J. M. de Bruin, Lionel Magna, Pascal Raybaud, Hervé Toulhoat, "Hemilabile Ligand Induced Selectivity: a DFT Study on Ethylene Trimerization Catalyzed by Titanium Complexes", Organometallics, 22, 3404-3413, 2003. We find: $Vm_0=0.201$ $nm^3$. The molecular volume of ethylene is calculated equal to $Vm_{C2=}=0.035$ $nm^3$.

Calculation of the molecular volume of the metallacycle intermediate, precursor of octene-1, thus gives $(Vm_0+4 Vm_{C2=})=0.341$ $nm^3$.

The calculation of $\Phi_{min}$ according to the prescribed formula gives: $\Phi_{min}=1.579 (Vm_o+Vm_M)^{1/3}-0.323=0.7805$ nm. We thus check that $\Phi$ is greater than $\Phi_{min}$, in this case $\Phi=1.063 \Phi_{min}$.

Example 3

According to the Invention

Oligomerization of Ethylene Catalyzed by the Teuben Complex $[(\eta^5\text{-}C_5H_4CMe_2C_6H_5)Ti^+]$ in the Presence of a Porous Solid of FAU Structure (Na—Y)

The procedure is the same as in Example 1, except for the initial introduction of 200 ml of a 5-mg/l Na—Y suspension in toluene instead of pure toluene. This solid was synthesized according to the operating mode described in the article by Hriljac, J. J., Eddy, M. M., Cheetham, A. K., Donohue, J. A. and Ray, G. J. *J. Solid State Chem.*, 106, 66-72 (1993). This material was subsequently entirely dehydrated and its porosity liberated by heating in an air stream for 2 hours at 300° C. Its chemical composition is then $Na_{58}Al_{58}Si_{134}O_{384}$. The amount added thus substantially corresponds to 15/192 micromoles of crystallized solid cells, i.e. substantially 1 constitutive cation ($Al^{3+}$ or $Si^{4+}$) per $Ti^+$ in the reaction medium.

The reaction is stopped after 60 seconds. Analysis of the reaction products shows that the hexene-1 productivity was multiplied by 1.75, thus substantially reaching 950 g per millimole of Ti per bar and per hour, whereas the octene-1 productivity substantially reaches 9540 g per millimole of Ti per bar and per hour (i.e. substantially 4.8 g $C_8$ products).

The average micropore diameter of the FAU structure is, as mentioned above, $\Phi=(0.74+1.18)/2=0.96$ nm.

Calculation of the molecular volume of the metallacycle intermediate, precursor of octene-1, gave (see Example 2) $(Vm_0+4 Vm_{C2=})=0.341$ $nm^3$.

The calculation of $\Phi_{min}$ according to the prescribed formula gives: $\Phi_{min}=1.579 (Vm_o+nVm_M)^{1/3}-0.323=0.7805$ nm. We thus check that $\Phi$ is greater than $\Phi_{min}$, in this case $\Phi=1.23 \Phi_{min}$.

Example 4

Not in Accordance with the Invention

Oligomerization of Ethylene Catalyzed by the Teuben Complex $[(\eta^5\text{-}C_5H_4CMe_2C_6H_5)Ti^+]$ in the Presence of a Porous Solid of MAZ Structure (Na—ZSM-4)

The procedure is the same as in Example 1, except for the initial introduction of 200 ml of a 5-mg/l Na—ZSM-4 suspension in toluene instead of pure toluene. This solid was synthesized in sodic form according to the operating mode described in U.S. Pat. No. 4,021,447. This material was subsequently entirely dehydrated and its porosity liberated by heating in an air stream for 2 hours at 300° C. Its chemical composition is then $Na_{10}Al_{10}Si_{26}O_{72}$. The amount added thus substantially corresponds to 15/36 micromoles of crystallized solid cells, i.e. substantially 1 constitutive cation ($Al^{3+}$ or $Si^{4+}$) per $Ti^+$ in the reaction medium.

The reaction is stopped after 30 minutes. Analysis of the reaction products shows that the hexene-1 and octene-1 productivity has not substantially varied in relation to the conditions without microporous solid introduction described in Example 1. The addition of the mazzite structure does not substantially modify the catalytic properties of the Teuben complex.

The average micropore diameter of the MAZ structure is, according to the IZA atlas, $\Phi=0.74$ nm.

Calculation of the molecular volume of the metallacycle intermediate, precursor of octene-1, gave (see Example 2) $(Vm_0 4 Vm_{C2=})=0.341$ $nm^3$.

The calculation of $\Phi_{min}$ according to the prescribed formula gives: $\Phi_{min}=1.579 (Vm_o+nVm_M)^{1/3}-0.323=0.7805$ nm. We thus find that $\Phi$ is less than $\Phi_{min}$, in this case $\Phi=0.948 \Phi_{min}$.

Example 5

According to the Invention

The procedure is the same as in Example 2, except for the initial introduction of 200 ml of a 46-mg/l AET suspension (AlPO-8) in toluene instead of pure toluene. The amount of solid added thus substantially corresponds to 150/72 micromoles of crystallized solid cells, i.e. substantially 10 constitutive cations ($Al^{3+}$ or $P^{5+}$) per $Ti^+$ in the reaction medium. The results obtained are substantially the same as in Example 2.

Example 6

According to the Invention

The procedure is the same as in Example 3, except for the initial introduction of 200 ml of a 2.5-mg/l Na—Y suspension in toluene instead of pure toluene. The amount of solid added thus substantially corresponds to 7.5/192 micromoles of crystallized solid cells, i.e. substantially 0.5 constitutive cation ($Al^{3+}$ or $Si^{4+}$) per $Ti^+$ in the reaction medium. The results obtained are degraded in relation to Example 3, the hexene-1 productivity substantially reaching only 700 g per millimole of Ti per bar and per hour, whereas the octene-1 productivity substantially reaches 7000 g per millimole of Ti per bar and per hour (i.e. substantially 3.5 g $C_8$ products).

Example 7

According to the Invention

Oligomerization of Ethylene Catalyzed by the Teuben Complex $[(\eta^5\text{-}C_5H_4CMe_2C_6H_5)Ti^+]$ in the Presence of ZIF-60 ZIF-60 $(Zn(IM)_{1.5}(mIM)_{0.5})$ The procedure is the same as in Example 1, except for the initial introduction of 200 ml of a 14.5-mg/l ZIF-60 Zn(Imidazolate) 1.5 (mehyl-imidazolate) 0.5 suspension (first activated by heating to 100° C. under primary vacuum for 24 hours) in toluene instead of pure toluene. This solid was synthesized and characterized according to an operating mode substantially identical to the one described in the article by Banerjee et al., "High Throughput Synthesis of Zeolitic Imidazolate Frameworks and Application to $CO_2$ Capture", Science, 319, 939-943, 2008 (Additional information). The chemical composition of this activated material is substantially $C_{11}H_{11}N_8Zn_2$. The amount added thus corresponds to 15/2 micromoles of crystallized solid cells, i.e. substantially 1 constitutive cation ($Zn^{2+}$) per $Ti^+$ in the reaction medium.

The reaction is stopped after 60 seconds. Analysis of the reaction products shows that the hexene-1 productivity was multiplied by 1.4, thus reaching 762 g per millimole of Ti per bar and per hour, whereas the octene-1 productivity is substantially multiplied by 440 and now reaches 293 g per millimole of Ti per bar and per hour (i.e. substantially 4.4 g $C_8$ products).

The average micropore diameter of the ZIF-60 structure is deduced from the data in the article by Banerjee et al. as the mean of the diameters of the pores (da) and of the cavities (dp) as defined in this article, and corresponding substantially to the definition according to the invention, i.e. $\Phi = (0.72+0.94)/2 = 0.83$ nm.

The molecular volume of the metallacycle intermediate, precursor of octene-1, is $(Vm_0+4\,Vm_{C2=}) = 0.341$ nm$^3$.

The calculation of $\Phi_{min}$ according to the prescribed formula gives: $\Phi_{min} = 1.579\,(Vm_o+nVm_M)^{1/3} - 0.323 = 0.7805$ nm. We thus check that $\Phi$ is greater than $\Phi_{min}$, in this case $\Phi = 1.063\,\Phi_{min}$.

Example 8

Not in Accordance with the Invention

Oligomerization of Ethylene Catalyzed by the Teuben Complex [($\eta^5$-$C_5H_4CMe_2C_6H_5$)$Ti^+$] in the Presence of ZIF-2 (Zn(IM)$_2$)

The procedure is the same as in Example 1, except for the initial introduction of 200 ml of a 15-mg/l ZIF-2 Zn(Imidazolate) 2 suspension (first activated by heating to 100° C. under primary vacuum for 24 hours) in toluene instead of pure toluene. This solid was synthesized and characterized according to an operating mode substantially identical to the one described in the article by Banerjee et al., "High Throughput Synthesis of Zeolitic Imidazolate Frameworks and Application to $CO_2$ Capture", Science, 319, 939-943, 2008 (Additional information). The chemical composition of this activated material is substantially $C_{12}H_{12}N_8Zn_2$. The amount added thus corresponds to 15/2 micromoles of crystallized solid cells, i.e. substantially 1 constitutive cation ($Zn^{2+}$) per $Ti^+$ in the reaction medium.

The reaction is stopped after 30 minutes. Analysis of the reaction products shows that the hexene-1 and octene-1 productivity has not substantially varied in relation to the conditions without microporous solid introduction described in Example 1. The addition of the ZIF-2 structure does not substantially modify the catalytic properties of the Teuben complex.

The average micropore diameter of the ZIF-2 structure is deduced from the data in the article by Banerjee et al. as the mean of da and dp as defined in this article, and corresponding substantially to the definition according to the invention, i.e. $\Phi = (0.64+0.69)/2 = 0.665$ nm.

The molecular volume of the metallacycle intermediate, precursor of octene-1, is $(Vm_0+4\,Vm_{C2=}) = 0.341$ nm$^3$.

The calculation of $\Phi_{min}$ according to the prescribed formula gives: $\Phi_{min} = 1.579\,(Vm_o+nVm_M)^{1/3} - 0.323 = 0.7805$ nm. We thus check that $\Phi$ is less than $\Phi_{min}$, in this case $\Phi = 0.852\,\Phi_{min}$.

Example 9

According to the Invention

Oligomerization of Ethylene Catalyzed by the Teuben Complex [($\eta^5$-$C_5H_4CMe_2C_6H_5$)$Ti^+$] in the Presence of IRMOF-1 [($Zn_4$O(Benzedicarboxylate)$_3$)]$_8$ The procedure is the same as in Example 1, except for the initial introduction of 200 ml of a 14.5-mg/l IRMOF-1 suspension (first activated by heating to 120° C. under primary vacuum for 24 hours) in toluene instead of pure toluene. This solid was synthesized and characterized according to an operating mode substantially identical to the one described in the article by Eddaoui et al., "Systematic Design of Pore Size and Functionality in Isoreticular MOFs and Their Application in Methane Storage", Science, 295, 469-472, 2002 (Additional information). The chemical composition of an elementary cell of this activated material is substantially $C_{192}H_{96}O_{104}Zn_{32}$. The amount added thus substantially corresponds to 15/32 micromoles of crystallized solid cells, i.e. substantially 1 constitutive cation ($Zn^{2+}$) per $Ti^+$ in the reaction medium.

The reaction is stopped after 30 minutes. Analysis of the reaction products shows that the hexene-1 productivity was multiplied by 1.2, thus reaching substantially 600 g per millimole of Ti per bar and per hour, whereas the octene-1 productivity is substantially multiplied by 36 and substantially reaches 24 g per millimole of Ti per bar and per hour (i.e. substantially 0.36 g $C_8$ products).

The average micropore diameter of the IRMOF-1 structure is deduced from the data in the article by Eddaoui et al. as the mean between the "fixed diameter" and the "free diameter" as defined in this article, and corresponding substantially to the definition according to the invention, i.e. $\Phi = (0.85+1.59)/2 = 1.22$ nm.

The molecular volume of the metallacycle intermediate, precursor of octene-1, is $(Vm_0+4\,Vm_{C2=}) = 0.341$ nm$^3$.

The calculation of $\Phi_{min}$ according to the prescribed formula gives: $\Phi_{min} = 1.579\,(Vm_o+nVm_M)^{1/3} - 0.323 = 0.7805$ nm. We thus check that $\Phi$ is greater than $\Phi_{min}$, in this case $\Phi = 1.56\,\Phi_{min}$.

Example 10

Not in Accordance with the Invention, Without Micro- or Mesoporous Solid

Dimerization of Butene-1 Catalyzed by a Pyridine Bisimine Iron Complex

We repeat, while adapting it to our equipment, the experiment described by B. R. Small and R. Schmidt, in the article "Comparative Dimerization of 1-Butene with a Variety of Metal Catalysts, and the Investigation of a New Catalyst for C—H Bond Activation", Chem. Eur. J. 2004, 10, 1014-1020, carried out with the iron complex denoted by 2 in this article, prepared according to the operating method described in the article by B. L. Small and M. Brookhart, J. Am. Chem. Soc. 1998, 120, 7143. The empirical formula of this complex is $C_{12}C_{23}H_{23}N_3Fe$, and its molar mass is substantially 468 g.mol$^{-1}$. Our experiment is carried out in a 1-litre autoclave and a U argon pressure of 10 bars is maintained above the liquid phase throughout the experiment. The co-catalyst is also MMAO 3A Akzo Nobel (modified methylaluminoxane). Substantially 10 mg of complex 2 (i.e. substantially 21 micromoles) are used for 250 g butene-1. The amount of MMAO 3A added corresponds to an Al/Fe molar ratio in the reaction medium substantially equal to 500. The reaction temperature is set at 30° C.±0.5° C. The reaction time is set at 3 hours. At the end of the reaction, substantially 125 g $C_8$ dimers are obtained, i.e. a 50% yield, substantially identical to the yield obtained by Small et al.

Example 11

According to the Invention

Dimerization of Butene-1 Catalyzed by a Pyridine Bisimine Iron Complex in the Presence of a Porous Solid of IRMOF-1 $[(Zn_4O(Benzedicarboxylate)_3)]_8$ structure The procedure is the same as in Example 10, except for the initial introduction of 50 ml of a 80-mg/l IRMOF-1 suspension (first activated by heating to 120° C. under primary vacuum for 24 hours) in pentane. The chemical composition of an elementary cell of this activated material is substantially $C_{192}H_{96}O_{104}Zn_{32}$. The amount added thus substantially corresponds to 4 mg, i.e. 21/32 micromoles of crystallized solid cells, i.e. substantially 1 constitutive cation ($Zn^{2+}$) per Fe in the reaction medium.

The reaction time is set at 30 mn. At the end of the reaction, substantially 200 g of $C_8$ dimers are obtained, i.e. an 80% yield. The productivity is thus multiplied by substantially 10.

The calculated molecular volume of the activated complex 2 is $Vm_0$=0.346 nm3. The calculated molecular volume of butene-1 is $Vm_{C4=}$=0.069 $nm^3$. Calculation of the molecular volume of the metallacycle intermediate, precursor of octene, thus gives ($Vm_0+2\ Vm_{C4=}$)=0.483 $nm^3$.

The calculation of $\Phi_{min}$ according to the prescribed formula gives: $\Phi_{min}$=1.579 $(Vm_o+nVm_M)^{1/3}$–0.323=0.917 nm. The mean diameter of the IRMOF-1 structure given in Example 9 is 1.22 nm. We thus check that $\Phi$ is greater than $\Phi_{min}$, in this case $\Phi$=1.33 $\Phi_{min}$.

Example 12

Not in Accordance with the Invention, without Micro- or Mesoporous Solid

Oligomerization of Ethylene Catalyzed by a Pyrollide Chromium Complex

We repeat, while adapting it to our equipment, Example III of U.S. Pat. No. 5,786,431 for preparing a chromium pyrrolide complex. This complex is used as an ethylene oligomerization catalyst according to an embodiment in accordance with Example VIII, "run 20", of the same patent, adapted to our equipment, described in Example 1. The pressure imposed during the oligomerization experiments is 38 bars (substantially 550 psig), and the temperature is 90° C.

The catalyst is prepared as indicated by dissolving substantially 0.2 g of the chromium complex in substantially 20 ml of a molar tri-ethyl-aluminium (TEA) solution, then by adding substantially 2 g aluminium phosphate $AlPO_4$ (substantially non microporous). After ripening under stirring, filtering, rinsing with toluene, then pentane, as indicated in the aforementioned patent, substantially 0.035 g of this catalyst is fed into the reactor, then 1 ml of a 0.5% solution of TEA in heptane, and finally 500 ml isobutane solvent.

Analysis of the reaction products shows substantially 99.5% liquids, including substantially 85% hexenes. The catalyst activity is substantially 2500 grams of product per gram of catalyst and per hour.

Example 13

According to the Invention

Oligomerization of Ethylene Catalyzed by a Pyrollide Chromium Complex in the Presence of the Neutral form of the AET Structure (ALPO-8)

The procedure is the same as in Example 12, except for the replacement of the 2 g of non-microporous aluminium phosphate by approximately 0.5 g of ALPO-8 solid used in Example 2. The (Al+P/Cr) ratio is thus set at substantially 6.

Analysis of the reaction products shows substantially 99.5% liquids, including substantially 80% $C_{14}$ oligomers. The catalyst activity is substantially multiplied by 6, reaching 15,000 grams of product per gram of catalyst and per hour.

The calculated molecular volume of the activated complex 2 is $Vm_0$=0.094 nm3. The calculated molecular volume of ethylene is, as indicated in Example 2, $Vm_{C2=}$=0.035 $nm^3$. Calculation of the molecular volume of the metallacycle intermediate, precursor of the $C_{14}$ linear oligomer, thus gives ($Vm_0+7\ Vm_{C2=}$)=0.339 $nm^3$.

The calculation of $\Phi_{min}$ according to the prescribed formula gives: $\Phi_{min}$=1.579 $(Vm_o+nVm_M)^{1/3}$–0.323=0.78 nm. The mean diameter of the AET structure given in Example 2 is 0.83 nm. We thus check that $\Phi$ is greater than $\Phi_{min}$, in this case $\Phi$=1.064 $\Phi_{min}$.

The invention claimed is:

1. A catalytic method of oligomerizing olefins M selectively to oligomers $M_n$, comprising selectively oligomerizing olefins M to oligomers $M_n$ by contacting said olefins M with a catalytic system comprising
   at least one organometallic complex of a metal of groups 4 to 10 of the periodic table of molecular volume $Vm_o$, and
   a microporous or mesoporous solid selected from the group consisting of zeolites, organic-inorganic hybrid materials, and mesoporous materials, whose pore diameter $\Phi$ expressed in nm is between $1.01*\Phi_{min}$ and $1.6*\Phi_{min}$, wherein $\Phi_{min}$ is defined as a function of the volume ($Vm_o+nVm_M$), expressed in $nm^3$, where n is the number of monomeric olefins strung together upon obtaining a metallacycle intermediate obtained through the contact between the olefins M and said organometallic complex of a metal of groups 4 to 10 of the periodic table, and $Vm_M$ is defined as the molecular volume of the monomeric olefin, wherein the relation between diameter $\Phi_{min}$ and volume ($Vm_o+nVm_M$) is as follows:

$$\Phi_{min}=1.579(Vm_o+nVm_M)^{1/3}-0.323,$$

wherein molecular volume Vm is defined as the volume delimited by the envelope surface of Van der Waals spheres centered on the atomic nuclei belonging to the organometallic complex and the olefin M in its geometry in the fundamental state as given by a crystallographic experiment or an ab initio theoretical calculation,
wherein
   oligomer $M_n$ is decene-1 and M is ethylene, or
   n is 14.
2. A method as claimed in claim 1, wherein the pore diameter $\Phi$ of said solid is between $1.05*\Phi_{min}$ and $1.25*\Phi_{min}$.
3. A method as claimed in claim 1, wherein said solid is a CFI, AFI, MAZ, AET, DON, FAU, CLO or VFI zeolite.

4. A method as claimed in claim 1, wherein said solid is an IRMOF or ZIF organic-inorganic hybrid material.

5. A method as claimed in claim 1, wherein said solid is an MOF of IRMOF-1 solid.

6. A method as claimed in claim 1, wherein said solid is a ZIF of ZIF-60 solid.

7. A method according to claim 1, comprising the oligomerization of ethylene catalyzed by the Teuben complex $[(\eta^5-C_5H_4CMe_2C_6H_5)Ti^+]$ in the presence of a porous solid of AET structure (ALPO-8).

8. A method according to claim 1, comprising oligomerization of ethylene catalyzed by the Teuben complex $[(\eta^5-C_5H_4CMe_2C_6H_5)Ti^+]$ in the presence of a porous solid of FAU structure (Na—Y).

9. A method according to claim 1, comprising oligomerization of ethylene catalyzed by the Teuben complex $[(\eta^5-C_5H_4CMe_2C_6H_5)Ti^+]$ in the presence of ZIF-60 $(Zn(IM)_{1,5}(mIM_{0,5}))$.

10. A method according to claim 1, comprising oligomerization of ethylene catalyzed by the Teuben $[(\eta^5-C_5H_4CMe_2C_6H_5)Ti^+]$ in the presence of IRMOF-1 $[Zn_4O(Benzedicarboxylate)_3)]_8$.

11. A method according to claim 1, comprising oligomerization of ethylene catalyzed by a pyrrolide chromium complex in the presence of the neutral form of the AET structure (ALPO-8).

12. A method according to claim 1, wherein said solid is MCM, SBA or carbon nanotubes.

13. A method according to claim 1, wherein oligomers $M_n$ is decene-1.

14. A catalytic method of oligomerizing olefins M selectively to oligomers $M_n$, comprising selectively oligomerizing olefins M to oligomers $M_n$ by contacting said olefins M with a catalytic system comprising
at least one organometallic complex of a metal of groups 4 to 10 of the periodic table of molecular volume $Vm_o$, and
a microporous or mesoporous solid selected from the group consisting of zeolites, organic-inorganic hybrid materials, and mesoporous materials, whose pore diameter $\Phi$ expressed in nm is between $1.01*\Phi_{min}$ and $1.6*\Phi_{min}$, wherein $\Phi_{min}$ is defined as a function of the volume $Vm_o+nVm_M$ expressed in nm³ where n is the number of monomeric olefins strung together upon obtaining a metallacycle intermediate obtained through the contact between the olefins M and said organometallic complex of a metal of groups 4 to 10 of the periodic table, and $Vm_M$ is defined as the molecular volume of the monomeric olefin, wherein the relation between diameter $\Phi_{min}$ and volume $(Vm_o+nVm_M)$ is as follows:

$$\Phi_{min}=1.579(Vm_o+nVm_M)^{1/3}-0.323,$$

wherein molecular volume Vm is defined as the volume delimited by the envelope surface of Van der Waals spheres centered on the atomic nuclei belonging to the organometallic complex and the olefin M in its geometry in the fundamental state as given by a crystallographic experiment or an ab initio theoretical calculation, and wherein n is 14.

* * * * *